US00PP08905P

United States Patent [19]

Drewlow

[11] Patent Number: Plant 8,905

[45] Date of Patent: Sep. 20, 1994

[54] IMPATIENS PLANT NAMED LARGO

[75] Inventor: Lyndon W. Drewlow, Ashtabula, Ohio

[73] Assignee: Mikkelsens, Inc., Ashtabula, Ohio

[21] Appl. No.: 163,762

[22] Filed: Dec. 9, 1993

[51] Int. Cl.[5] ..... A01H 5/00

[52] U.S. Cl. ..... Plt./87.6

[58] Field of Search ..... Plt. 87.6

*Primary Examiner*—James R. Feyrer

*Attorney, Agent, or Firm*—Foley & Lardner

[57] ABSTRACT

A new and distant cultivar of Impatiens plant named Largo, characterized by its double flower form having ten petals, scarlet red flower color, flower diameter of 5.5 to 6.0 cm, reddish-purple flower spurs, green pedicels, six leaves in a whorl, continuous flowering above leaf canopy, medium green foliage with yellow-green midrib and no variegation, highly self-branching and floriferous habit, ability to tolerate both high and low temperature, and its adaptability to production in 10 cm up to 15–25 cm pots.

2 Drawing Sheets

The present invention relates to a new and distinctive cultivar of Impatiens plant, botanically known as Impatiens, commercially known as New Guinea Impatiens, and known by the cultivar name Largo.

The new cultivar was developed in a controlled breeding program conducted by the inventor Lyndon W. Drewlow in Ashtabula, Ohio. Largo was created by crossing Mikkelsen Seedling No. 90-1095-1 (seed parent) with Mikkelsen Seedling No. 90-1054-1 (pollen parent). Both parents are proprietary cultivars used in the breeding program.

Asexual reproduction by terminal or stem cuttings carried out by or under the supervision of the inventor at Ashtabula, Ohio has shown that the unique features of this new Impatiens are stabilized and are reproduced true to type in successive propagations.

The following combination of characteristics distinguish the new Impatiens from both its parent varieties and other cultivated Impatiens of this type known and used in the floriculture industry. The description includes reference to comparison cultivars Mirach, disclosed in U.S. Plant Pat. No. 6,309, and Baroque, disclosed in a pending application of the inventory.

1. Largo is a representative of an entirely new class of New Guinea Impatiens that have ten flower petals, double the number of petals of single-flower types such as Mirach. Baroque is another cultivar in the double-flowered group.

2. Largo has scarlet red flower color (47A) while the flower color of Mirach is a more organge red (42A). Baroque has a purple rose flower color.

3. Largo has a flower diameter of 5.5 to 6.0 cm, larger than either Baroque (4.5 to 5.0 cm) or Mirach (5.0 to 5.5 cm).

4. The flower spur of Largo is reddish purple with a green tip, while Mirach has a deeper reddish purple spur with a reddish tip and Baroque has a slight reddish tint to the spur and a green tip.

5. Largo has green flower pedicels with a reddish cast near the end where the pedicels are attached to the flower. Mirach has a reddish-purple pedicel and Baroque has a green flower pedicel.

6. Largo has a solid green leaf with a glabrous upper surface, while Mirach has a cream variegated leaf with a slightly hirsute upper leaf surface, and Baroque has a solid green hirsute upper leaf surface.

7. The leaf length (9.0 cm) of Largo is similar to both Mirach and Baroque, but Largo has a wider leaf (3.5 to 4.0 cm) compared to Mirach (2.5 to 3.0 cm) and Baroque (3.0 to 3.5 cm).

8. Largo has mostly green stems with a trace of reddish cast near the nodes. Mirach has reddish-purple stems and Baroque is intermediate in red pigmentation in the stems.

9. Both Largo and Baroque are 5 to 7 days later to bloom than Mirach as it take the double flowers with ten petals longer to develop and open than five petals of the single-flowered Mirach.

10. Largo has a green area around the midrib on the backside of the standard petal while Mirach has only a small area of green on the rib of the standard petal, and Baroque has green extending well into the petal area.

11. Both Largo and Baroque are much more self-branched than Mirach.

In the photographic drawings, the color photo at the top illustrates in perspective view the overall appearance of Largo, with the colors being as true as it is reasonably possible to obtain in a color reproduction of this type. The color photo was taken on Sep. 24, 1993 under natural light under 40% saran in a shaded glass greenhouse in Ashtabule, Ohio on a sunny day. The black and white photo on the bottom shows three (3) views of a typical flower of the new cultivar.

The following is a detailed description of my new cultivar, based on plants produced in greenhouses in Ashtabula, Ohio during the summer season of the year. Plants were grown in 15 cm pots and measurements were taken 18 weeks after rooted cutting were planted. Height measurements were taken from the soil line of the container. The plants were grown at 65°–68° F. night temperatures under 3000–4000 foot candles of light and with 250 ppm nitrogen, 75 ppm potassium, and 250 ppm phosphorous nutritional levels, with trace elements added. Habit of growth, foliage coloration, leaf variegation, size of leaves and flower size will be influenced by nutritional and environmental conditions, without, however, any variance in the genotype.

Color references are made to the Royal Horticultural Society Colour Chart except where general terms of ordinary dictionary significance are used.

Parentage: A controlled cross between female parent Mikkelsen Seedling No. 90-1095-1 and male parent Mikkelsen Seedling 90-1054-1.

Propagation:

(A) *Type cutting.*—Stem tip is 15 mm long and will develop 4 to 5 cm long in 18 to 21 days.

(B) *Time to root.*—8–10 days at 23° C. summer; 10–12 days at 20° C. winter.

(C) *Rooting habit.*—Heavy, fibrous.

Plant description:

(A) *Form and habit of growth.*—Semi-upright, self-branched, intermediate in height, flowers above leaf canopy; continuous flowering; vigorous growing herb.

(B) *Foliage.*—Deep green with yellow-green mid-rib; no variegation. (1) Size: 8.5 to 9.5 cm long and 3.5 to 4.0 cm wide for average mature leaf. (2) Shape: Lanceolate with acuminate apex and acute base. (3) Texture: Both upper and lower surfaces are glabrous. (4) Margin: Finely serrated with fine ciliate. (5) Color: Young foliage, top side is 146A; under side is 147C; mature foliage, top side is 147A; under side is 148C. (6) Veination: Pinnate, green veins.

Flowering description:

(A) *Flowering habits.*—Flowers continuously from leaf whorl in a progressively orderly manner with usually two flowers per leaf axil. All first flowers in a whorl open before the second flower in the leaf axil of that whorl start to open. When second flowers of a leaf axil start to open the first flowers of a leaf axil of whorl above starts to open. It takes 5 to 7 days for a mature bud to fully open and then the flower may last two weeks or longer depending on the environment.

(B) *Natural flowering season.*—Indeterminant and continuous. Quantity of flowering increases with increasing levels of light.

(C) *Flower buds.*—Ellipsoidal, flowers perfect; reddish-purple spur with green tips 4.5 cm long on mature bud, with throat behind the ovary and originating from the major sepal.

(D) *Flowers borne.*—On individual 3.5 to 4.0 cm green pedicels with reddish cast near end attached to flower, from a whorl of usually 6 leaves flowering progressively around the whorl as buds and leaves develop. Two flowers per leaf axil is normal.

(E) *Quantity of flowers.*—Highly floriferous because of self-branching nature of plant, two flowers per leaf axil, and long lasting flowers.

(F) *Diameter of flower.*—5.5 to 6.0 cm.

(G) *Petals.*—(1) Shape: Heart, keel petals of bottom whorl of petals are the largest. (2) Color: Top side in summer when opening is 47A, fading to 47B; under side is 47B. (3) Number of petals: Ten. (4) Type of petals: Standard: Both whorls have a standard petal; Wings: Two sets of wing petals; Keel: Two sets of keel petals.

(H) *Reproductive organs.*—(1) Stamens: Five (5) in number. (a) Anther: Hooded shape; color is red. (b) Pollen color: Cream. (2) Pistils: (a) Stigma shape: Five (5), segmented column; color is greenish yellow. (b) Style color: Greenish yellow. (c) Ovaries: Five (5) in number; size is 5 mm when mature; color is green.

Disease resistance: No significant insect or disease problems to date.

OTHER IMPORTANT CHARACTERISTICS

1. Self-branching characteristic, and semi-upright habit and intermediate height make Largo suitable for 10 cm pot production, but cultivar is vigorous enough for 15 and 25 cm pot production as well.

2. Largo can withstand both high temperatures and sunlight as well as low temperatures (40° to 50° F.), thus extending the outside growing season and locations the cultivar can be planted.

3. The ten petal flowers result in a fuller flower as compared to the normal five petal flower types. Thus, a double-flowered plant with the same number of flowers as a single-flowered plant is substantially more colorful.

I claim:

1. A new and distinct cultivar of Impatiens plant named Largo, as illustrated and described.

* * * * *

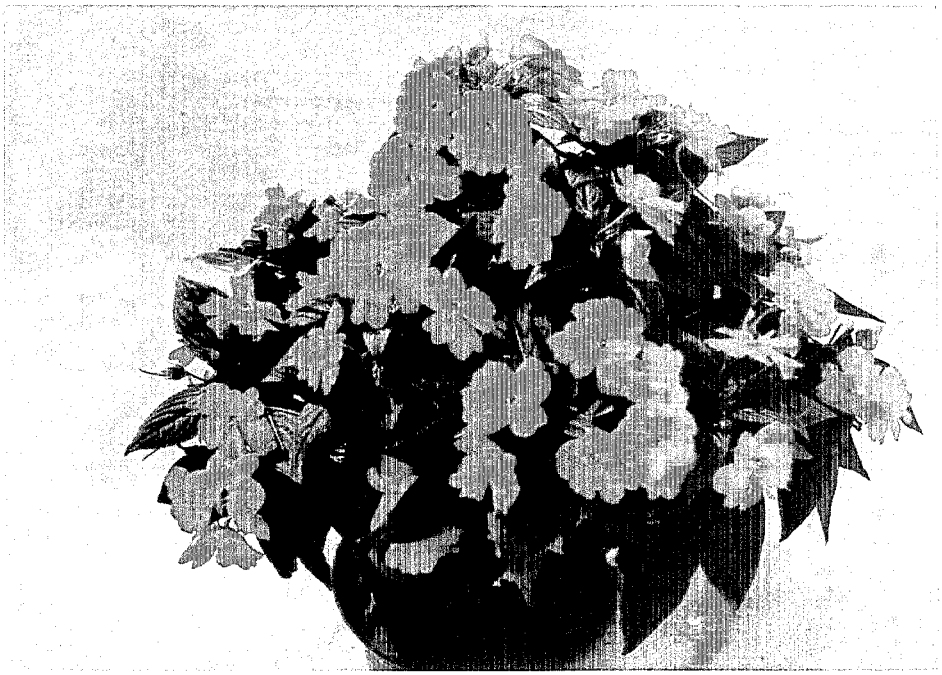

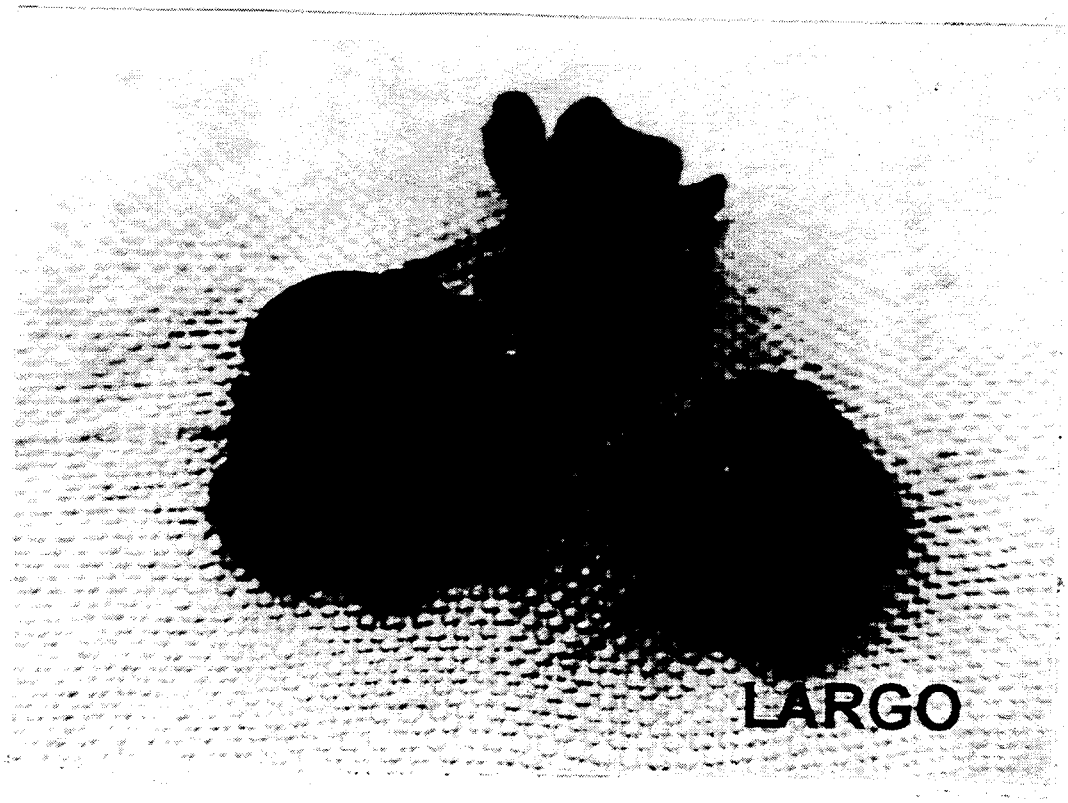
LARGO